United States Patent [19]

Lees

[11] 4,397,531
[45] Aug. 9, 1983

[54] EYE CLOSURE DISCRIMINATION SYSTEM

[75] Inventor: David E. B. Lees, Lexington, Mass.

[73] Assignee: Honeywell Inc., Minneapolis, Minn.

[21] Appl. No.: 278,525

[22] Filed: Jun. 29, 1981

[51] Int. Cl.³ ............................................. A61B 3/14
[52] U.S. Cl. .................................. 351/210; 351/211; 351/221; 340/575; 340/576
[58] Field of Search ............... 351/210, 211, 221, 237, 351/206; 340/575, 576

[56] References Cited

U.S. PATENT DOCUMENTS 2,726,380 12/1955 Campisi ............................... 351/158
3,462,604 8/1969 Mason .
4,149,787 4/1979 Kobayashi et al. .

Primary Examiner—John K. Corbin
Assistant Examiner—Paul M. Dzierzynski

[57] ABSTRACT

A system for determining whether an eye within a field of view is closed for a predetermined period of time and for distinguishing between reflections from an open eye and any specular reflections within the field of view. The system comprises detection apparatus for viewing the field of view. Also included is a first light source positioned so that light arising from the light source causes reflections from both an open eye and from any specular reflectors within the field of view to be detected by the detection apparatus. The system further includes a second light source positioned so that light arising from the light source causes reflections from the open eye to be directed so as not to be detected by the detection apparatus and so that light arising from the light source causes reflections from any specular reflectors in the field of view to be directed so as they are detected by the detection apparatus. The detection apparatus comprises apparatus for comparing over a predetermined period of time the number of reflections arising from the first and second light sources. If the number of reflections arising from the first and second light sources during the predetermined period of time are equal, it is assumed that the eye was closed for the predetermined period of time.

10 Claims, 6 Drawing Figures

EYE CLOSURE DISCRIMINATION SYSTEM

BACKGROUND OF THE INVENTION

The present invention is a system for determining whether an eye within a field of view is closed for a predetermined period of time and for distinguishing between an open eye and any specular reflectors within the field of view. Although the present invention is disclosed as part of an alertness monitor system, it is not limited to such applications.

In manufacturing environments requiring the use of heavy machinery in dark or dimly lit areas, for example, in the confines of a mine it is useful to provide a system to monitor and maintain driver alertness. Ideally, such a system might consist of a device which sets off an alarm when the subject closes his eyes for a period greater than some predetermined length of time. Such a system might also be used for a variety of commercial applications, for example, as a remote eye-controlled switch.

The operational object of an alertness monitor is to detect and distinguish the presence of an open eye in some specific field of view and to discriminate between eye blinks and the condition of sleep. A prior art eye fundus camera described in U.S. Pat. No. 4,149,787 provides a means to detect eye closure. However, unlike the present invention, it requires proximity of the eye to the device, only provides a limited field of view, and does not have provision to discriminate between the eye and other bright objects within that field of view. In addition, also unlike the present invention, it relies on the principle that under certain forms of illumination the eye lid will reflect more light than the eye itself.

In addition, there are many prior art systems which track eye motion or relate the line of sight of the eye to some coordinate system. In one such device, an oculometer described in U.S. Pat. No. 3,462,604, a source is used to illuminate an area which contains the subject's head. The light reflected off the back surface of the eye through the pupil creates a bright spot, much like a cat's-eye retroreflector. If a television camera or other imaging device is placed along the boresight of the source to record scene illumination, the location of the bright spot, in relation to other reflections off the eye, can be used to determined the line of sight of the eyes.

In the embodiment disclosed, the present invention uses a variation of this optical technique, termed bright pupil illumination, to remotely determine eye presence. Briefly, the disclosed system uses a pair of switched sources to provide consecutive pairs of images with and without bright pupil illumination by which the subject's eyes can be distinguished from self-luminous objects or specular reflections off glasses or other objects in the scene. An alarm is set off when the subject closes his eyes longer than a predetermined length of time.

SUMMARY OF THE INVENTION

The present invention is a system for determining whether an eye within a field of view is closed for a predetermined period of time and for distinguishing between reflections from an open eye and any specular reflections within the field of view. The system comprises detection apparatus for viewing the field of view. Also included is a first light source positioned so that light arising from the light source causes reflections from both an open eye and from any specular reflectors within the field of view to be detected by the detection apparatus. The system further includes a second light source positioned so that light arising from the light source causes reflections from the open eye to be directed so as not to be detected by the detection apparatus and so that light arising from the light source causes reflections from any specular reflectors in the field of view to be directed so as they are detected by the detection apparatus. The detection apparatus comprises apparatus for comparing over a predetermined period of time the number of reflections arising from the first and second light sources. If the number of reflections arising from the first and second light sources during the predetermined period of time are equal, it is assumed that the eye was closed for the predetermined period of time.

DESCRIPTION OF THE PREFERRED EMBODIMENT

Figure 1:
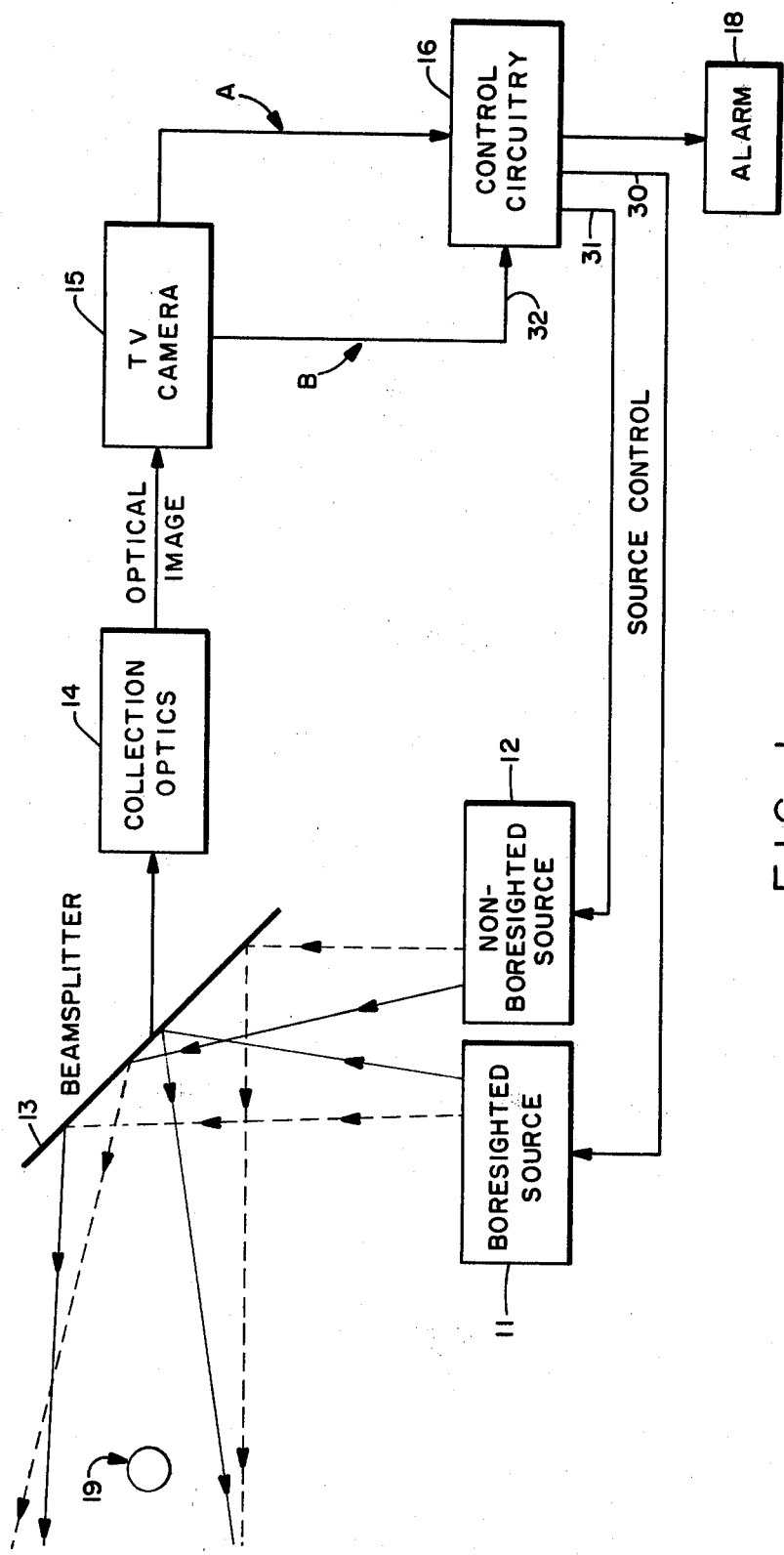
FIG. 1 schematically illustrates a preferred embodiment of an alertness motion system employing the present invention.
Figure 2A:
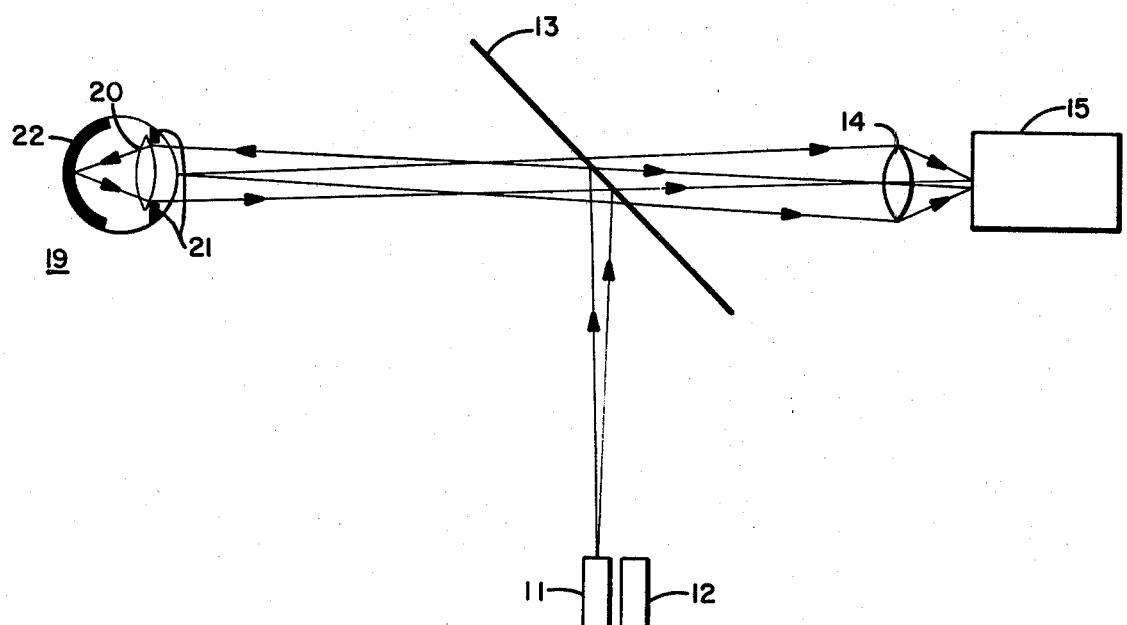
FIG. 2A shows a path of light from a boresighted light source reflected from an eye through a beamsplitter to collection optics of the disclosed system.
Figure 2B:
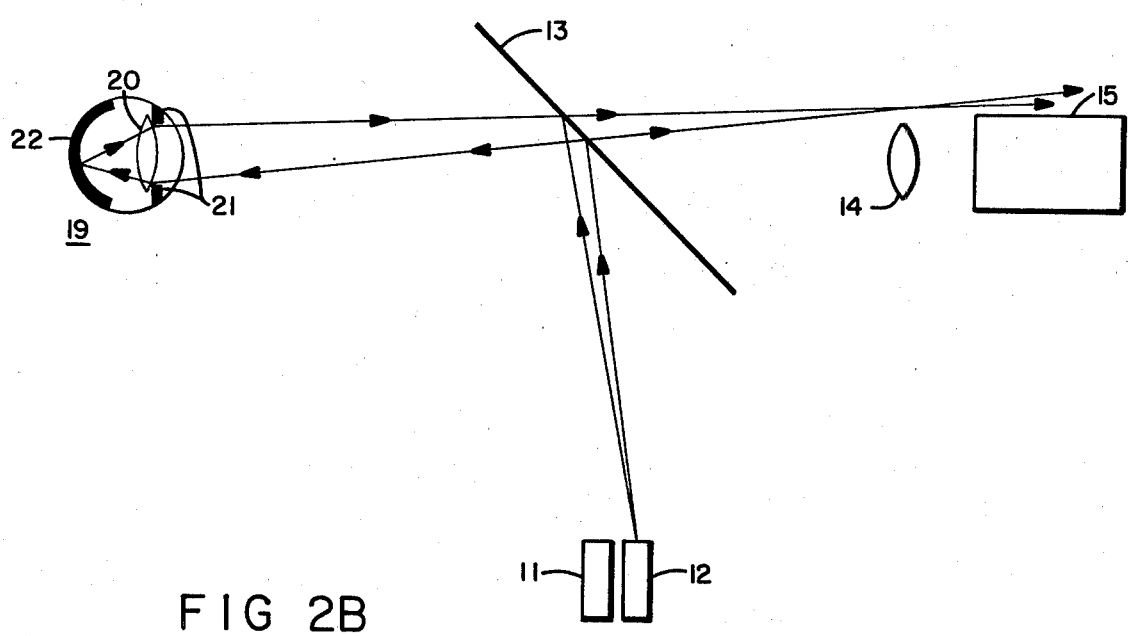
FIG. 2B shows a path of light from a non-boresighted source reflected from the eye through the beamsplitter so that it misses the collection optics of the system.

In FIGS. 2A and 2B an eye 19 is schematically shown as consisting of a roughly spherical cavity with a lens 20 and pupil 21 and lined by a retinal surface 22. Light from either of two sources 11 and 12 is projected onto the area of interest by reflection off a beamsplitter 13. This light is focused by lens 20 of eye 19 onto retina 22. A certain amount of light will reflect off retina 22 and be transmitted back through both lens 20 and beamsplitter 13.

In this configuration, the eye functions like a retroreflector, a reflector which sends a reflected ray back along the same path as a corresponding incident ray. Thus, a beam of light from boresighted source 11 which enters the eye at some angle and reflects off retinal surface 22 will exit the eye along the same path and will be imaged at video camera 15.

As shown, sources 11 and 12 are placed side by side at an angle of approximately 45 degrees to the normal of beamsplitter 13 so that they illuminate approximately the same volume surrounding the subject's head. FIGS. 2A and 2B show the arrangements of sources 11 and 12, beamsplitter 13, and collection optics 14 at video camera 15 so that the reflected real image of a source created by boresighted illumination falls inside the aperture of collection optics 14 (FIG. 2A) while the image of a source caused by non-boresighted illumination will fall outside collection optics 14 (FIG. 2B).

In the preferred embodiment of the alertness monitor disclosed, two gallium arsenide light emitting diodes are used as illumination sources at a wavelength of 0.93 microns. These provide enough flux (0.1 mw/cm$^2$) to create bright pupil illumination without causing eye damage (for example, retinal burns or cataracts) and have the added advantage that they do not distract the subject, since they operate at a near infrared wavelength.

In the system as disclosed, sources 11 and 12 are placed side by side, approximately 100 cm from the intended subject area, so that both sources illuminate the same region, a volume of approximately 27000 cm$^3$ around the subject's head. Actual subject distance is arbitrary, but in this embodiment 100 cm was selected as the average distance between a driver and the dashboard of the vehicle. Irradiance at the subject distance (0.1 mw/cm$^2$) is significantly lower than in accepted safety regulations. As a further safety precaution, a shield is placed around sources 11 and 12 to limit the minimum distance between subject and sources to 15 cm. Collection optics 14, in this example, comprise a standard photographic lens, which focuses and relays the scene image to video camera 15, which may comprise a Telemation 1100 video camera with an SIT tube operating at 60 fields per second.

In operation of the present system, sources 11 and 12 are used to alternately illuminate the area of interest, camera 15 being placed along the boresight of one source to record each illuminated scene. The switching of boresighted source 11 and non-boresighted source 12 is synchronized with the operation of camera 15 so that consecutive video frames display the scene illuminated by either source. A video output signal A of camera 15 is passed through an analog comparator within control circuitry 16 so that the number of pulses in signal A greater than a threshold value can be recorded for each type of source illumination. The system then relies on the difference in video image content between the scene illuminated by the boresighted and non-boresighted sources.

For example, when a subject's eyes are open, the video image of the scene illuminated by boresighted source 11 will contain bright pupils. No bright pupils can appear in the image of the scene illuminated by non-boresighted source 12 because the retroreflected image of the bright pupils will fall outside collection optics 14 of camera 15. The scene illuminated by boresighted source 11 will then have more threshold crossings when the eyes are open because it contains the image of bright pupils. Therefore, if the number of threshold crossings for the two scenes is different, it is assumed that the eyes are present and open; if they are the same, then the eyes are closed or not present in the illuminated scene.

Figure 4:
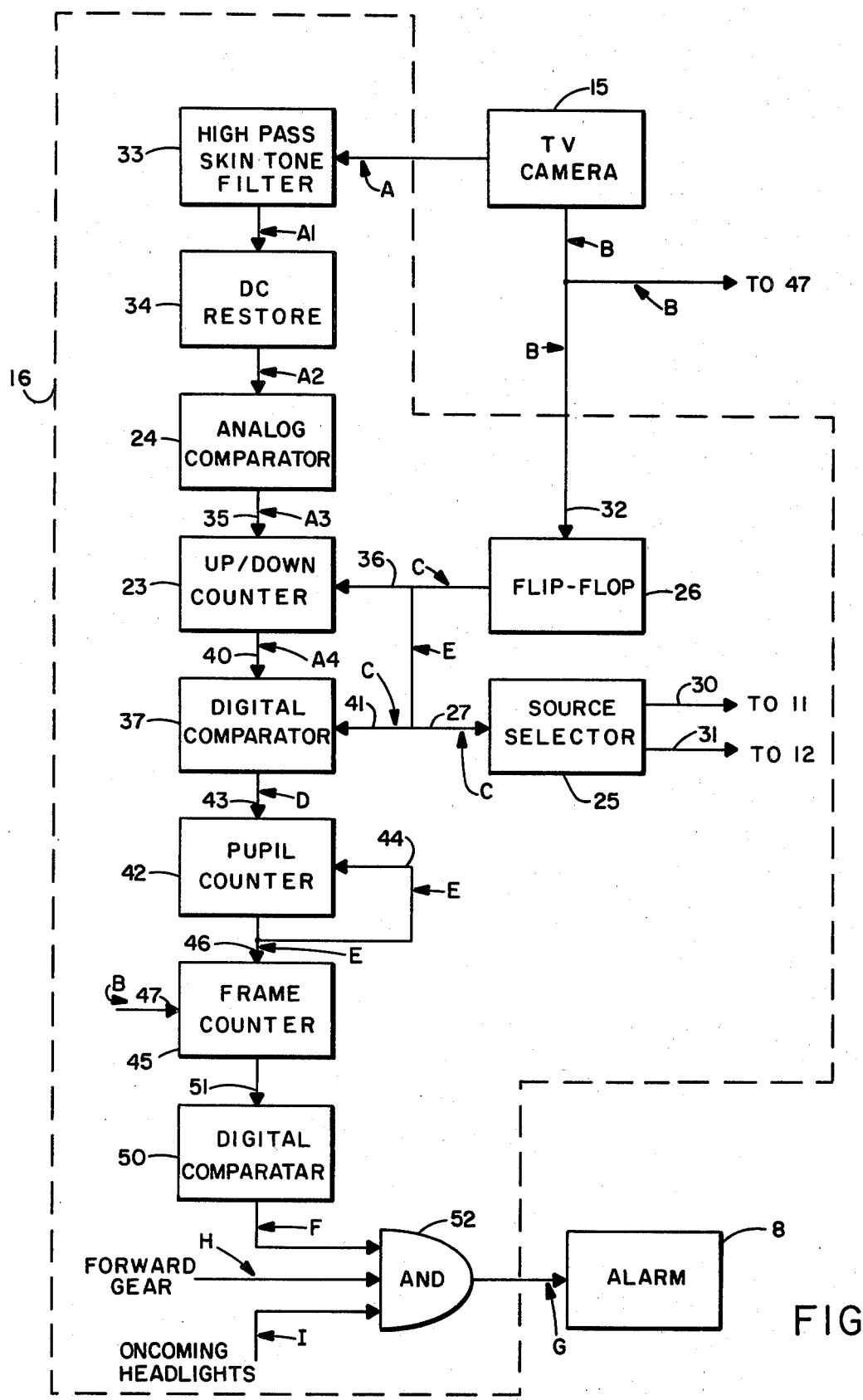
FIG. 4 illustrates circuitry compatible with the disclosed system.

Control circuitry 16 compatible with the present invention is illustrated in FIG. 4. In the present system as disclosed, one of two sources 11 or 12 is always on. A source selector 25 is connected to a flip-flop 26 via an input 27. Selector 25, which may comprise 2N6284 switching transistors, is fed a two-state control signal C from flip-flop 26 which may comprises a 7474 or 74107. When control signal C at source selector input 27 is high, non-boresighted source 12 is off, and boresighted source 11 is turned and held on via an output signal from source selector output 30. When control signal C at input 27 is low, boresighted source 11 is off, and non-boresighted source 12 is turned and held on via a signal from output 31 of source selector 25. Flip-flop 26 is connected to camera 15 via an input 32. The two states of flip-flop 26 are changed whenever input 32 receives a pulse derived from a camera sync signal B.

Figure 3A:
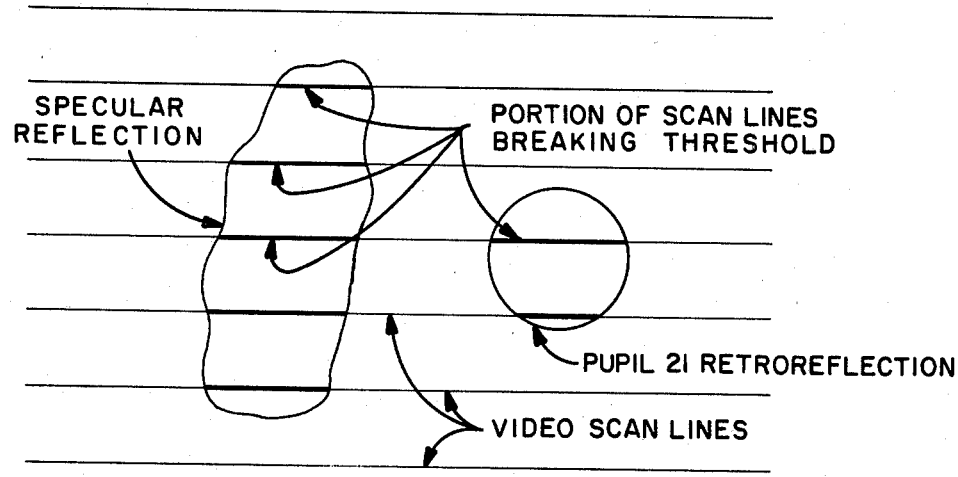
FIG. 3A shows portions of television camera scan lines breaking threshold for a video image of a boresight-illuminated subject wearing goggles.
Figure 3B:
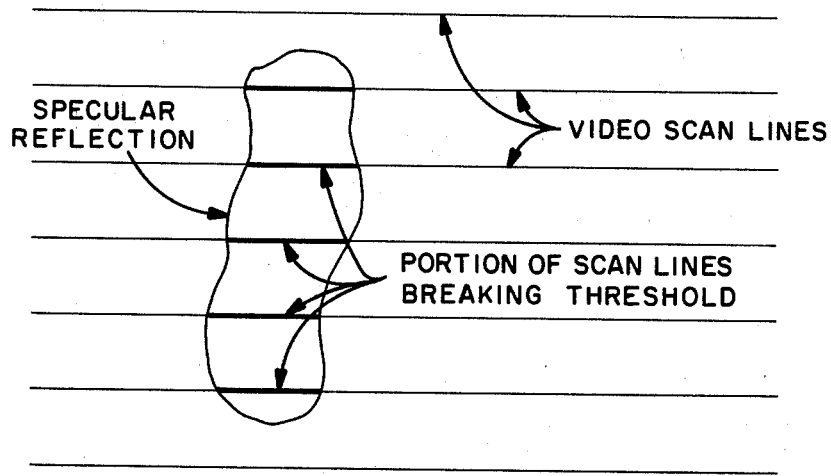
FIG. 3B shows portions of scan lines breaking threshold for the corresponding video image of a non-boresight-illuminated subject wearing goggles.

Camera video output signal A is sent through a high pass active filter 33 to remove variations in skin tones (filter 33 may comprise an HA2515). Filter 33 provides a processed analog signal A1 which is DC restored by DC restore 34 which may comprise a transistor circuit to ground the video briefly at the start of each video line to avoid DC drift. DC restored analog signal A2 is then processed through threshold comparator 24 so that a count can be made each time signal A2 exceeds a pupil threshold value for a particular frame. For example, in the case of an operator wearing safety glasses or goggles, a typical image under boresighted illumination might provide many threshold crossings since the bright pupils and specular reflections of the glasses would cover an area more than one scan line thick in the video image. FIGS. 3A and 3B show two corresponding video images of a subject with goggles illuminated by boresighted and non-boresighted sources respectively.

An output from comparator 24 feeds an input 35 of an up/down counter 23. When video signal A2 exceeds the pupil threshold, a two-state output signal A3 of comparator 24 goes high. Up/down counter 23, which may comprise a 74193, is a device which counts low to high transitions at input 35. Each input transition causes counter 23 to increment or decrement depending on the state at an up/down input 36 (whether counter 23 is incrementing or decrementing is also referred to as its count direction state).

The count direction state of counter 23 is set at input 36 which is connected to flip-flop 26, the same flip-flop which determines which source 11 or 12 is turned on as previously explained. When flip-flop 26 output signal C is high, counter 23 counts up. When signal C is low, counter 23 counts down.

Digital comparator 37, which may comprise a Signetics 8242, is coupled to up/down counter 23 via an input 40 and to flip-flop 26 via an input 41. Input 40 receives a signal A4 from counter 23 whenever the result of an up/down count cycle is not equal to zero. Comparator 37 generates an output signal D when gated by a high to low transition in signal C from flip-flop 26, the high to low transition indicating that a complete up/down counting cycle has been completed, and when the result of an up/down count cycle is not equal to zero.

A pupil counter 42 receives signal D via an input 43 connected to the counter, signal D being received every time an up/down count cycle indicates a pupil being present. Counter 42, which may comprise a 74161, is initiated to a negative number, −N. When counter 42 is incremented N times indicating N cycles with a pupil present, its content reaches zero and a pulsed output signal E is generated. Signal E is provided to a reset input 44 to counter 42 to reset the counter to −N. Signal E is also provided to a frame counter 45 via an input 46 to clear counter 45. Frame counter 45, which may also comprise a 74161, is incremented by start-field pulses within signal B derived from camera 15, signal B being received by counter 45 via an input 47. Counter 45 is connected to a digital comparator 50 via an input 51. The contents of counter 45 are compared by digital comparator 50 with a constant M. When the value of frame counter 51 reaches M, comparator 50 generates and holds an output control signal F which indicates the pupil has not been seen a sufficient number of times in the last M video fields. Then, assuming that the vehicle in which the disclosed device is placed is in forward gear, thus providing a control signal H, and that there are no on-coming head lights, thus providing a control signal I, AND gate 52 generates an alarm or control signal G which may turn on an alarm 8 or other means to wake the driver.

The present invention is to be limited only in accordance with the scope of the appended claims since others skilled in the art may devise other embodiments still within the limits of the claims. For example, as previously indicated, the present invention need not take the form of an alertness monitor, but rather could be in the form of an eye switch or other control mechanism.

The embodiments of the invention in which an exclusive property or right as claimed are defined as follows:

1. A system for determining whether an eye within a field of view is closed for a predetermined period of time and for distinguishing between reflections from an open eye and any specular reflections within the field of view, comprising:
   detection means for viewing the field of view;
   a first light source positioned so that light arising from the light source causes reflections from both an open eye and from any specular reflectors within the field of view to be detected by the detection means;
   a second light source positioned so that light arising from the light source causes reflections from the open eye to be directed so as not to be detected by the detection means and so that light arising from the light source causes reflections from any specular reflectors in the field of view to be directed so as to be detected by the detection means;
   the detection means comprising means for comparing over a predetermined period of time the number of reflections arising from the first and second light sources;
   whereby, if the number of reflections arising from first and second light sources are equal during the predetermined period of time, it is assumed that the eye was closed for the predetermined period of time.

2. The apparatus of claim 1 wherein the detection means comprises means for alternately sequencing the first and second light sources.

3. The apparatus of claim 2 wherein the detection means comprises a beamsplitter for reflecting light from the first and second light sources into the field of view and for transmitting reflected light to the detection means.

4. The apparatus of claim 3 wherein the detection means comprises means for providing a first control signal if the eye is closed for the predetermined period of time.

5. The apparatus of claim 4 wherein the detection means further comprises means for requiring the presence of a second control signal occurring concurrently with the first control signal before a third control signal is generated.

6. The apparatus of claim 1 wherein the detection means comprises a beamsplitter for reflecting light from the first and second light sources and into the field of view and for transmitting reflected light to the detection means.

7. The apparatus of claim 6 wherein the detection means comprises means for providing a first control signal if the eye is closed for the predetermined period of time.

8. The apparatus of claim 7 wherein the detection means further comprises means for requiring the presence of a second control signal occurring concurrently with the first control signal before a third control signal is generated.

9. The apparatus of claim 1 wherein the detection means comprises means for providing a first control signal if the eye is closed for the predetermined period of time.

10. The apparatus of claim 9 wherein the detection means further comprises means for requiring the presence of a second control signal occurring concurrently with the first control signal before a third control signal is generated.

* * * * *